(12) United States Patent
Park et al.

(10) Patent No.: US 9,764,639 B2
(45) Date of Patent: Sep. 19, 2017

(54) SINGLE LINK TYPE DRIVE ASSISTANCE SYSTEM FOR HANDICAPPED PERSON

(71) Applicants: Hyundai Motor Company, Seoul (KR); Hakrhim Machinery Co., Seoul (KR)

(72) Inventors: Sang-Don Park, Anyang-si (KR); Heui-Geon Lee, Anyang-si (KR); Han Bae, Suwon-si (KR); Ki-Soo Kim, Seongnam-si (KR)

(73) Assignees: Hyundai Motor Company, Seoul (KR); Hakrhim Machinery Co., Seoul (KR)

( * ) Notice: Subject to any disclaimer, the term of this patent is extended or adjusted under 35 U.S.C. 154(b) by 344 days.

(21) Appl. No.: 14/559,767

(22) Filed: Dec. 3, 2014

(65) Prior Publication Data

US 2016/0052390 A1    Feb. 25, 2016

(30) Foreign Application Priority Data

Aug. 19, 2014 (KR) .................. 10-2014-0107602

(51) Int. Cl.
*B60K 20/00* (2006.01)
*B60K 26/02* (2006.01)
(Continued)

(52) U.S. Cl.
CPC .............. *B60K 26/02* (2013.01); *B60T 7/102* (2013.01); *G05G 1/04* (2013.01); *B60K 2026/028* (2013.01)

(58) Field of Classification Search
CPC ... B60K 26/02; B60K 2026/028; B60T 7/102; G05G 1/04
See application file for complete search history.

(56) References Cited

U.S. PATENT DOCUMENTS 1,353,379 A * 9/1920 Caulfeild ............... B60K 26/02
74/481
2,523,491 A * 9/1950 Auten ..................... B60K 26/02
477/170
(Continued)

FOREIGN PATENT DOCUMENTS

JP          09-39600 A      2/1997
JP          3057214 U      12/1998
(Continued)

*Primary Examiner* — Zakaria Elahmadi
(74) *Attorney, Agent, or Firm* — Morgan, Lewis & Bockius LLP

(57) ABSTRACT

A single link type drive assistance system for a handicapped person may include a control bar configured to make a hinge joint connected to a steering column to form a rotation center at time of up and down operations at a lower portion of a steering wheel, a pedal operation link configured to include an inner tube connected to the control bar to deliver a down operation force using a brake pedal and an outer tube surrounding the inner tube, the outer tube moving along with the inner tube at the time of the down operation to operate the brake pedal and slidably moving with respect to the inner tube without a motion of the inner tube connected to the brake pedal at the time of the up operation, and an accelerator cable unit applied with a sliding motion of the outer tube to operate an accelerator pedal.

13 Claims, 8 Drawing Sheets

(51) Int. Cl.
*B60T 7/10* (2006.01)
*G05G 1/04* (2006.01)

(56) References Cited

U.S. PATENT DOCUMENTS

| | | | | |
|---|---|---|---|---|
| 2,731,850 | A | * | 1/1956 | Otto et al. .............. B60K 26/02 200/61.54 |
| 2,747,427 | A | * | 5/1956 | Morsch .................. B60K 26/02 477/193 |
| 4,722,416 | A | * | 2/1988 | Ahnafield ............. B60W 30/18 180/333 |
| 5,947,227 | A | * | 9/1999 | Kempf .................. B60W 30/18 180/335 |
| 6,237,711 | B1 | * | 5/2001 | Hunt ..................... B60W 30/18 180/315 |
| 6,263,753 | B1 | * | 7/2001 | Froehlich ................ B60T 7/02 180/333 |
| 6,898,995 | B1 | * | 5/2005 | Schonlau ............... B60K 26/02 74/512 |
| 8,141,669 | B1 | * | 3/2012 | Laymaster ........... B60K 7/0007 180/216 |
| 2004/0227339 | A1 | * | 11/2004 | Davis .................... B60K 26/02 280/771 |
| 2005/0200112 | A1 | * | 9/2005 | Berg ...................... B60K 26/02 280/775 |
| 2008/0269015 | A1 | * | 10/2008 | Ochiai ................... B60K 26/02 477/209 |
| 2009/0026001 | A1 | * | 1/2009 | Shaum .................. B60K 26/02 180/333 |
| 2011/0079473 | A1 | * | 4/2011 | Revelis .................. B60T 7/102 188/2 D |
| 2014/0245858 | A1 | * | 9/2014 | Johnson ................... G05G 1/04 74/523 |
| 2014/0251071 | A1 | * | 9/2014 | Ben-Dor ................. G05G 1/04 74/523 |

FOREIGN PATENT DOCUMENTS

| | | |
|---|---|---|
| JP | 2004-291950 A | 10/2004 |
| JP | 2004-353569 A | 12/2004 |
| JP | 2007-045384 A | 2/2007 |
| KR | 10-2008-0042646 A | 5/2008 |
| KR | 20-2013-0005252 U | 8/2013 |

* cited by examiner

A single link type drive assistance system for a handicapped person may include a control bar configured to make a hinge joint connected to a steering column to form a rotation center at the time of up and down operations at a lower portion of a steering wheel, a pedal operation link configured to include an inner tube connected to the control bar to deliver a down operation force using a brake pedal and an outer tube surrounding the inner tube, the outer tube moving along with the inner tube at the time of the down operation to operate the brake pedal and slidably moving with respect to the inner tube without a motion of the inner tube connected to the brake pedal at the time of the up operation, and an accelerator cable unit configured to be applied with the sliding motion of the outer tube to operate an accelerator pedal.

SINGLE LINK TYPE DRIVE ASSISTANCE SYSTEM FOR HANDICAPPED PERSON

CROSS-REFERENCE TO RELATED APPLICATIONS

The present application claims priority to Korean Patent Application No. 10-2014-0107602, filed on Aug. 19, 2014, which is incorporated herein by reference in its entirety.

BACKGROUND OF THE INVENTION

Field of the Invention

Exemplary embodiments of the present invention relate to a drive assistance system for a handicapped person, and more particularly, to a single link type drive assistance system for a handicapped person with improved convenience and appearance by operating an accelerator and a brake with one link.

Description of Related Art

Today, a drive assistance system for a handicapped person is based on a method of operating an accelerator and a brake by the hand to be able to drive a vehicle without operating them by the foot.

As an example, there is a drive assistance system for a handicapped person configured to include a control bar which may be operated by the hand, an accelerator link configured of an outer/inner tube and connected to an accelerator pedal arm, and a brake link configured of an outer/inner tube and connected to a brake pedal arm.

According to the drive assistance system for a handicapped person, when a handicapped person pulls a handle of the control bar, the accelerator link is pushed downward based on a bearing and thus a force is delivered a pedal through the link, such that the accelerator pedal is pressed to make acceleration. At the time of operating the accelerator, the brake link gets out by making the outer tube be slid from the inner tube and thus an operation of the brake pedal is not changed. To the contrary, when a handicapped person pushes the handle of the control bar forward, a force is delivered through the brake line to push the pedal and thus the brake pedal is operated, such that braking is made. At the time of operating the brake, the accelerator link gets out by making the outer tube be slid from the inner tube and thus an operation of the brake pedal is not changed.

Therefore, a handicapped person pulls or pushes the handle of the control bar to control the accelerator and the brake, such that he/she may drive a vehicle.

However, the drive assistance system for a handicapped person has an insufficient design from the perspective of a handicapped person, and therefore a lot of inconvenience may be caused.

As the example, operation noise which brings about customer complaints due to an excessive "clank" noise generated when the two links are slid during the operation of the drive assistance system and operation inconvenience which makes it difficult to perform elaborate acceleration due to a pedal ratio reduced at the time of acceleration or deceleration and requires an excessive force at the time of braking since the links are fixed to the pedal arm may be caused.

As another example, the drive assistance system may not be mounted at the time of applying a flow mount type accelerator pedal, and thus may be hardly applied to various pedal specifications.

First of all, low collision stability which fatally damages driver's face, chest, etc. due to a breakage of two links at the time of collision cannot but increase a risk of safety accidents of a handicapped person having coping capabilities lower than those of a normal person.

In particular, when considering that the number of handicapped persons registered in the country is constantly increasing to 2004 (1,610,000)→2008 (2,240,000)→2012 (2,510,000), there is a need to improve a drive assistance system for a handicapped person in which an accelerator link for acceleration and a brake link for braking are each configured in one control bar for operation in an independent double link type.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a single link type drive assistance system for a handicapped person with improved collision stability, noise, and operability even when a vehicle is driven with a normal person on board, in particular, with more improved marketability due to beautiful appearance provided in a state in which a shroud is actually mounted, by controlling an accelerator and a brake using one link.

Other objects and advantages of the present invention can be understood by the following description, and become apparent with reference to the exemplary embodiments of the present invention. Also, it is obvious to those skilled in the art to which the present invention pertains that the objects and advantages of the present invention can be realized by the means as claimed and combinations thereof.

In accordance with an exemplary embodiment of the present invention, a single link type drive assistance system for a handicapped person includes, a control bar configured to make a hinge joint connected to a steering column to form a rotation center at the time of up and down operations at a lower portion of a steering wheel; a pedal operation link configured to include an inner tube connected to the control bar to deliver a down operation force using a brake pedal and an outer tube surrounding the inner tube, the outer tube moving along with the inner tube at the time of the down operation to operate the brake pedal and slidably moving with respect to the inner tube without a motion of the inner tube connected to the brake pedal at the time of the up operation; and. an accelerator cable unit configured to be applied with the sliding motion of the outer tube to operate an accelerator pedal.

The accelerator cable unit may receive the sliding motion of the outer tube through a cable of a nylon material and the cable of a nylon cable may have flexibility and length to absorb the motion of the outer tube along with the inner tube.

The control bar may be provided with a handle having a button disposed at an opposite side of the hinge joint, the hinge joint may be connected by a column bracket and a hinge bearing fixed to the steering column, and the column bracket and the hinge bearing may be covered with a column tube surrounding the steering column.

The pedal operation link may be connected to the control bar by an upper ball joint of the inner tube and may be connected to the brake pedal using a brake pedal bracket fixed to a lower ball joint of the inner tube.

The brake pedal bracket may be configured to include a pedal operation link fixing part fixed to the lower ball joint, a pedal arm fixing part fastened with an arm portion of the brake pedal, and a brake pad flange pressed to a pad portion of the brake pedal. The pedal operation link fixing part and the pedal arm fixing part may be each fastened with each other by a bolt and the brake pad flange may surround the pad portion.

The accelerator cable unit may be configured to include an accelerator link cable of a nylon material having flexibility and a length to absorb the motion of the outer tube along with the inner tube and receiving the sliding motion of the outer tube, an accelerator link receiving the motion of the accelerator link cable, an accelerator pedal cable delivering the motion of the accelerator link to an accelerator pedal bracket, and an accelerator link bracket maintaining a tension of the accelerator link.

The accelerator link cable may be provided with an accelerator link damper flange coupled with the outer tube and the accelerator link damper flange may be connected to the cable of a nylon material to be connected to the accelerator link. The accelerator link damper flange may have a '⊓'-letter shape to make the cable of a nylon material be spaced apart from the outer tube. The accelerator link damper flange may be further provided with a guide of a plastic material and have a '⊏'-letter shape.

The accelerator link may be configured to include an accelerator link cable connection part connected to the cable of a nylon material and an accelerator pedal cable connection part connected to the accelerator pedal cable and the accelerator link cable connection part and the accelerator pedal cable connection part may be each configured of a ball joint.

The accelerator pedal cable of the nylon material may be connected to the accelerator pedal cable connection part of the accelerator link and the accelerator link bracket may be provided with an accelerator pedal damper fixed by a screw.

The accelerator link bracket may be provided with an accelerator link ball joint supporting the accelerator pedal cable and may be provided with an accelerator link bracket fixing part fixed to a vehicle body panel at which the steering column is located.

The accelerator pedal bracket may be fixed by the accelerator pedal damper of the accelerator pedal cable and the screw and may be provided with an accelerator pad flange fitted in a pad portion of the accelerator pedal.

The control bar and the pedal operation link may be exposed to the outside from a shroud panel surrounding a circumference of the steering column.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
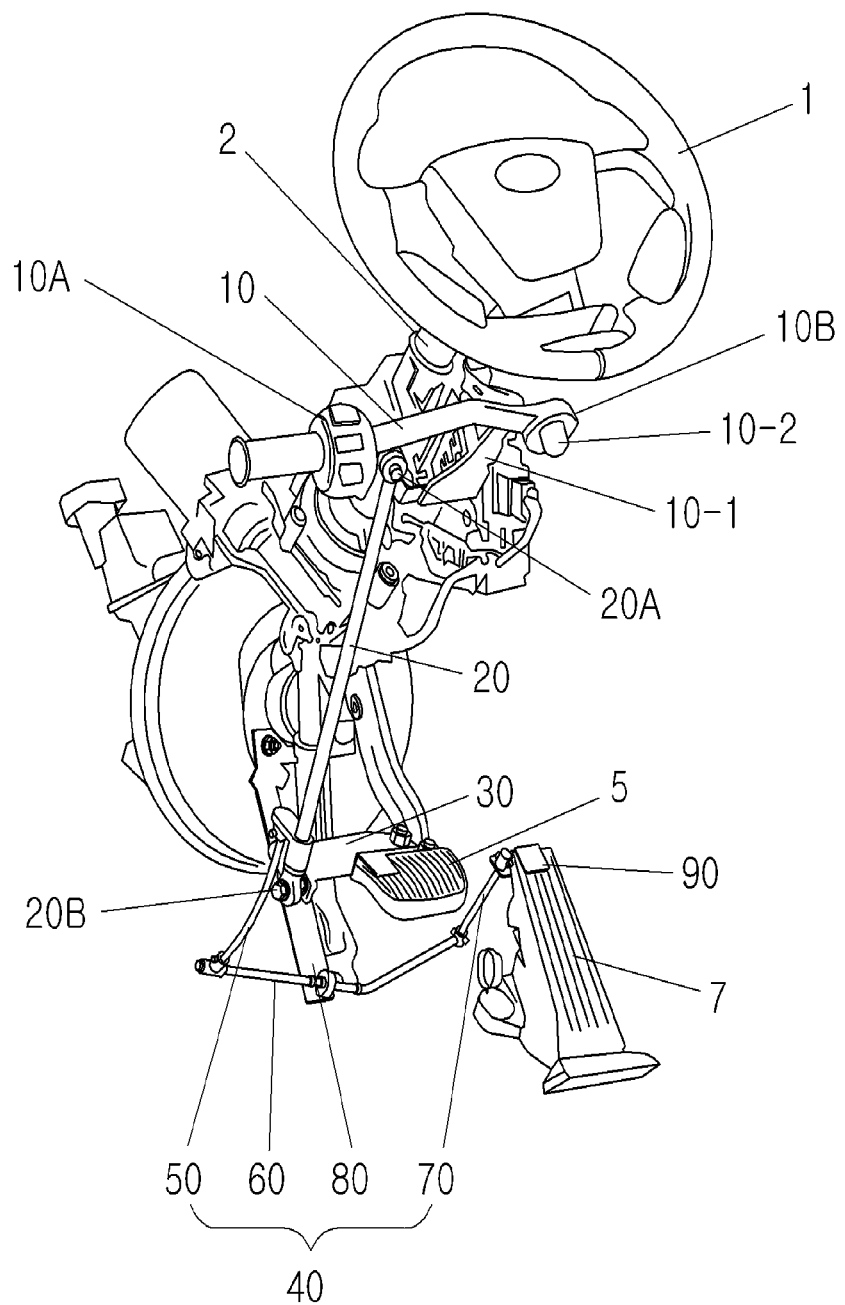
FIG. 1 is a configuration diagram of a single link type drive assistance system for a handicapped person according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DESCRIPTION OF SPECIFIC EMBODIMENTS

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

FIG. 1 illustrates a configuration of a single link type drive assistance system for a handicapped person according to an exemplary embodiment of the present invention.

As illustrated in FIG. 1, the drive assistance system includes a control bar 10 configured to be located under a steering wheel 1; a pedal operation link 20 configured to deliver a brake operation of the control bar 10 to a brake pedal 5; a brake pedal bracket 30 configured to be connected to a motion of the pedal operation link 20 to operate the brake pedal 5; an accelerator cable unit 40 configured to deliver an accelerator operation of the control bar 10 to an accelerator pedal 7; and. an accelerator pedal bracket 90 configured to be connected to a motion of the accelerator cable unit 40 to operate the accelerator pedal 7.

One portion of the control bar 10 is provided with a handle 10A having a button (for example, direction indicator) operated by a driver's finger and the other portion thereof is provided with a hinge joint 10B configured to be hinge-connected to a steering column 2 under the steering wheel 1.

The pedal operation link 20 is connected to the control bar 10 using a lower ball joint 20A and is connected to the brake pedal bracket 30 using a lower ball joint 20B.

The brake pedal bracket 30 is connected to the pedal operation link 20 to deliver the motion of the pedal operation link 20 to the lower ball joint 20B and is connected to the brake pedal 5 to operate the brake pedal 5 with the motion of the pedal operation link 20 delivered to the lower ball joint 20B.

The accelerator cable unit 40 includes an accelerator link cable 50 configured to separate the accelerator operation of the control bar 10 from the pedal operation link 20; an accelerator link 60 configured to receive the motion of the accelerator link cable 50; an accelerator pedal cable 70 configured to deliver the motion of the accelerator link 60 to the accelerator pedal bracket 90; and. an accelerator link bracket 80 configured to maintain a tension of the accelerator link 60. In particular, the accelerator link cable 50 which has a damping structure for noise prevention and is coupled with the pedal operation link 20 delivers an accelerator operation force to the accelerator link 60 through a rope type cable of a nylon material and forms a leverage structure for the lower ball joint 20A of the pedal operation link 20. The accelerator link 60 is connected to the accelerator link cable 50 and the accelerator pedal cable 70, respectively, through a ball join as a medium. The accelerator pedal cable 70 delivers the accelerator operation force to the accelerator pedal bracket 90 through the rope type cable of a nylon material. The accelerator link bracket 80 is fixed to a vehicle body panel at which the steering column 2 is located and is connected to the accelerator link 60 through the ball joint as a medium to maintain the tension of the accelerator link 60.

The accelerator pedal bracket 90 is connected to the accelerator pedal 7 to operate the accelerator pedal 7 with the motion of the accelerator pedal cable 70.

Meanwhile, FIGS. 2 to 5 each illustrate a connection structure of the control bar 10, the pedal operation link 20, the brake pedal bracket 30, the accelerator cable unit 40, and the accelerator pedal bracket 90.

Figure 2:
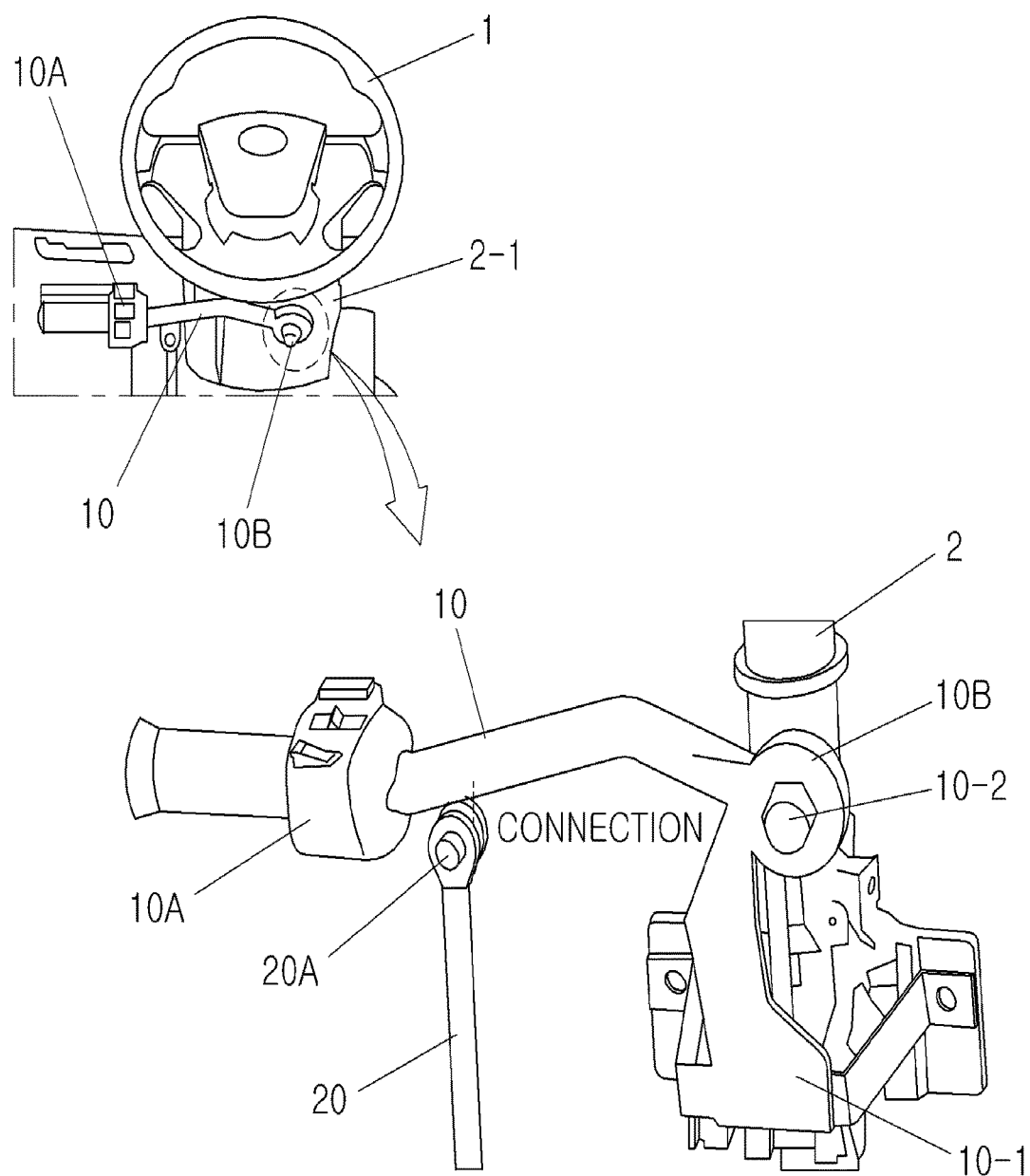
FIG. 2 is a diagram illustrating a connection structure between a control bar and a steering column according to an exemplary embodiment of the present invention.

Referring to FIG. 2, a connection portion between the control bar 10 and the steering column 2 is covered with a column tube 2-1 which surrounds the steering column 2, a column bracket 10-1 fixed to the steering column 2 inside the column tube 2-1 is hinge-connected to the hinge joint 10B, and a connection portion between the hinge joint 10B and the column bracket 10-1 is provided with a hinge bearing 10-2 to make the operation of the control bar 10 smooth.

Figure 3:
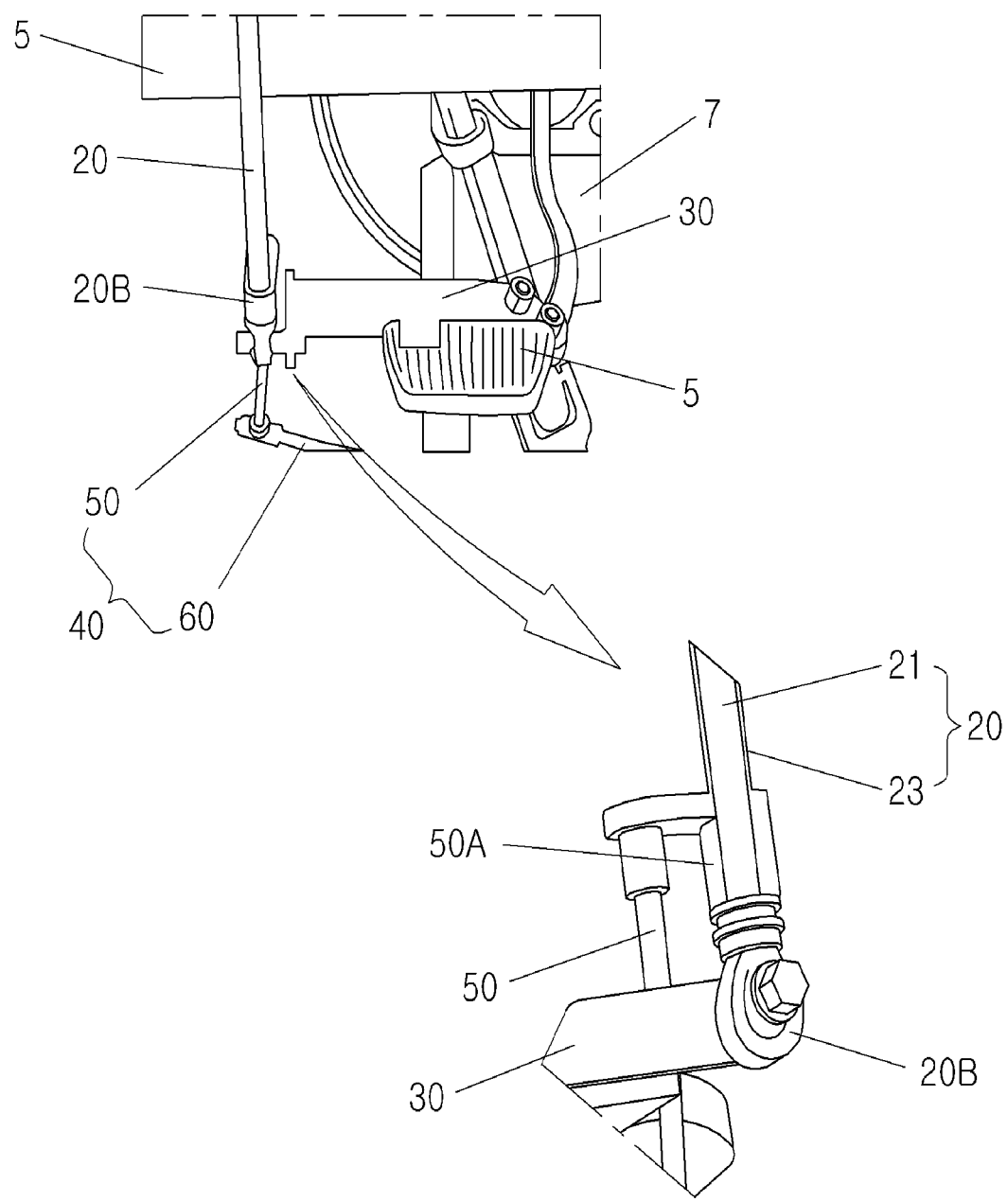
FIG. 3 is a connection structure of a pedal operation link according to an exemplary embodiment of the present invention.

Referring to FIG. 3, the pedal operation link 20 includes an inner tube 21 configured to include an upper ball joint 20A connected to the control bar 10 and a lower ball joint 20B connected to the brake pedal bracket 30 and an outer tuber 23 configured to surround the inner tube 21 and be connected to the accelerator link cable 50. In particular, an upper end of the outer tube 23 is fixed to the upper ball joint 20A, while a lower end thereof is separated from the lower ball joint 20B, thereby forming a double tube structure in which the outer tube 23 may be slid with respect to the inner tube 21.

The slidable double tube structure forms a sliding motion of separating the outer tube 23 from the lower ball joint 20B when the pedal operation link 20 moves upward by pulling the control bar 10 to pull the accelerator link cable 50 without operating the brake pedal 5, in which an operation force of the accelerator link cable 50 is delivered to the operation force of the accelerator pedal 7 via the accelerator link 60, the accelerator pedal cable 70, and the accelerator pedal bracket 90.

Figure 4:
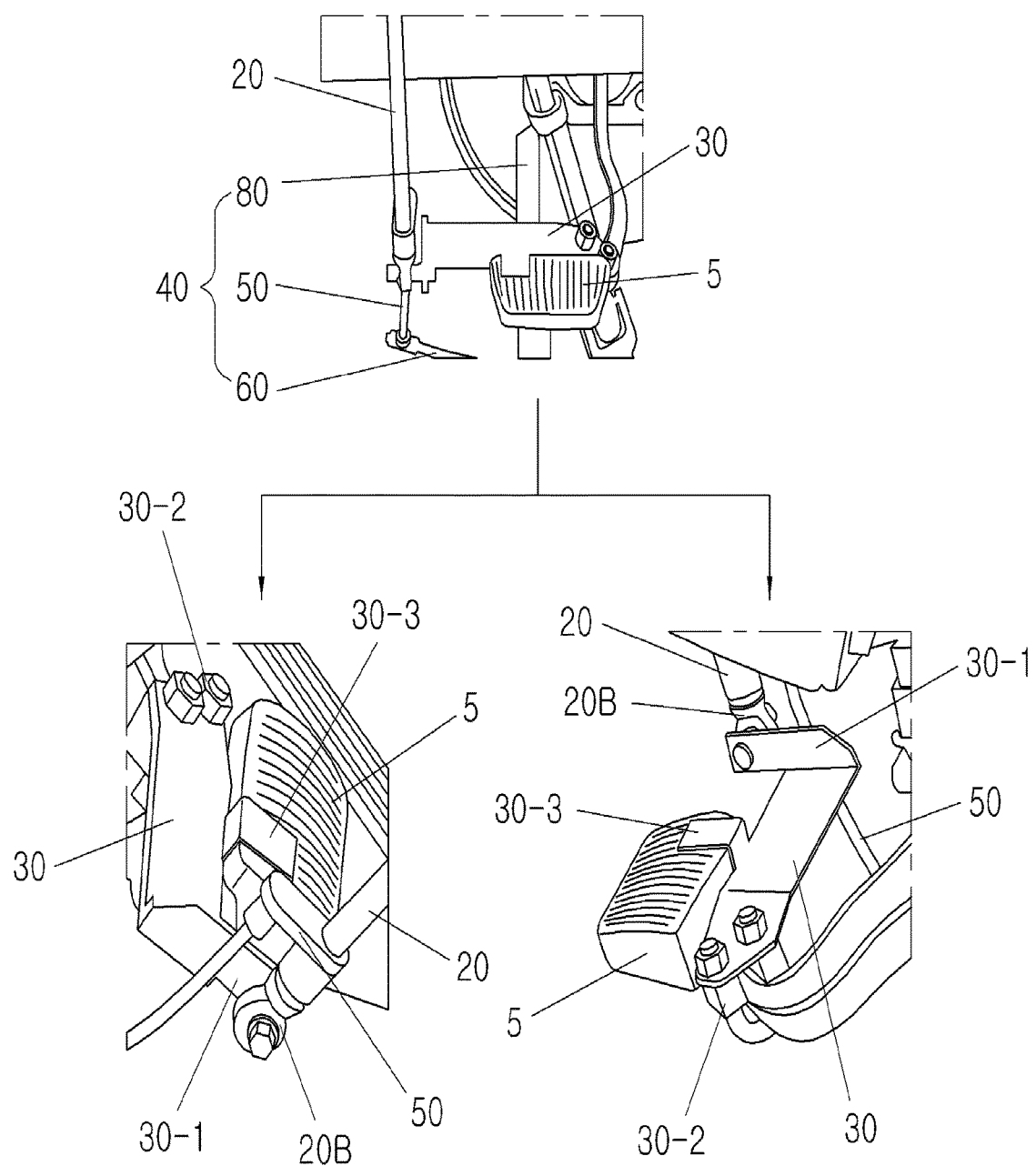
FIG. 4 is a diagram illustrating a brake pedal bracket connection structure of the pedal operation link according to an exemplary embodiment of the present invention.

Referring to FIG. 4, the brake pedal bracket 30 includes a pedal operation link fixing part 30-1 configured to fix the lower ball joint 20B formed in the inner tube 21 of the pedal operation link 20 and the brake pedal bracket 30, a pedal arm fixing part 30-2 configured to fasten the brake pedal bracket 30 with an arm portion of the brake pedal 5, and a brake pad flange 30-3 configured to locate the brake pedal bracket 30 at a pad portion of the brake pedal 5. To this end, the pedal operation link fixing part 30-1 and the pedal arm fixing part 30-2 are each fastened by a bolt. In particular, the brake pad flange 30-3 prevents the brake pedal bracket 30 from deforming and pedal operation feeling from reducing even in a length of the slightly longer brake pedal bracket 30 by pressing the pad portion of the brake pedal 5 in the state in which the brake pad flange 30-3 surrounds the pad portion of the brake pedal 5 pressed to the pedal arm fixing part 30-2.

Figure 5:
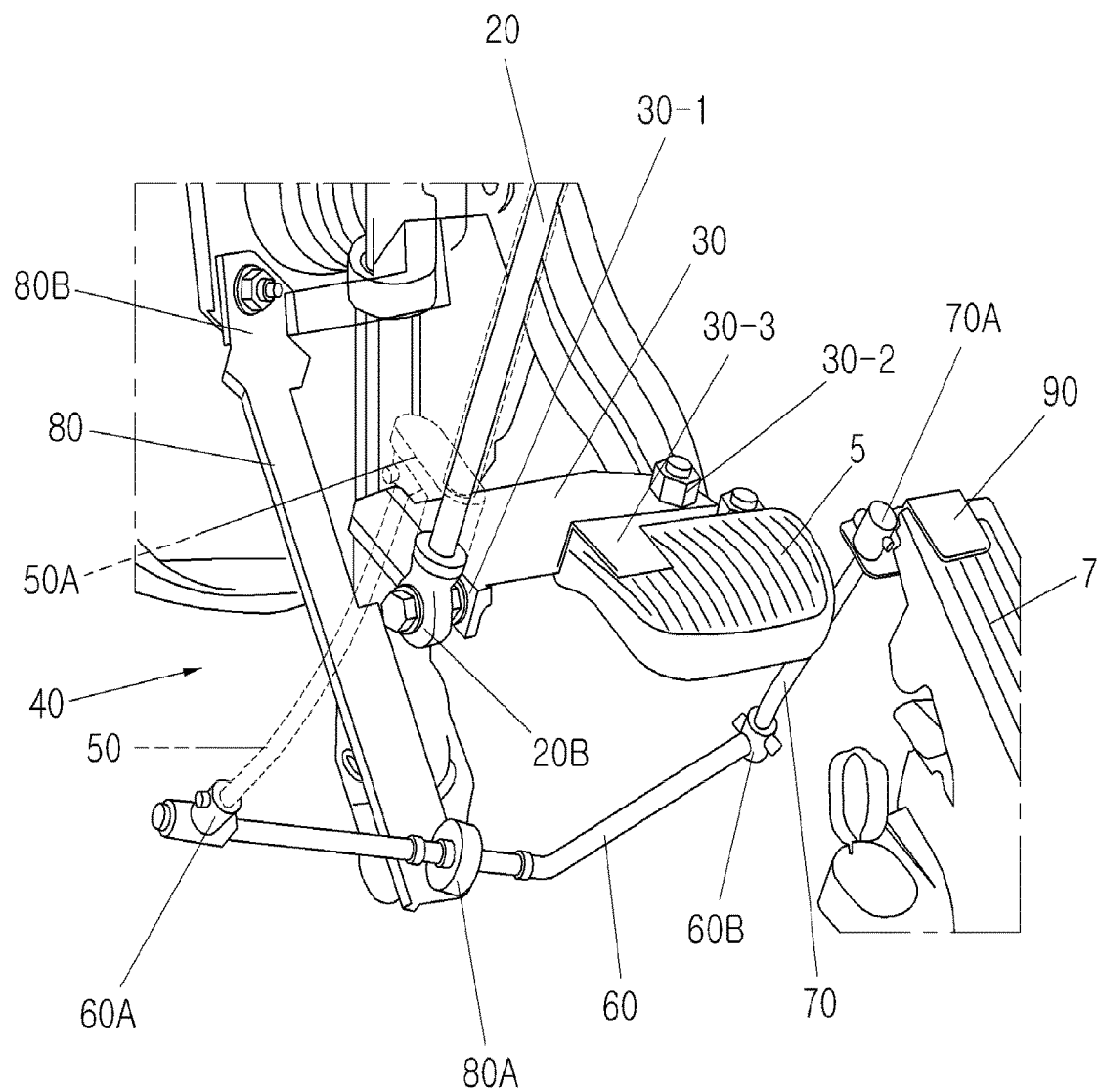
FIG. 5 is an accelerator cable structure of the pedal operation link according to an exemplary embodiment of the present invention.
Figure 6:
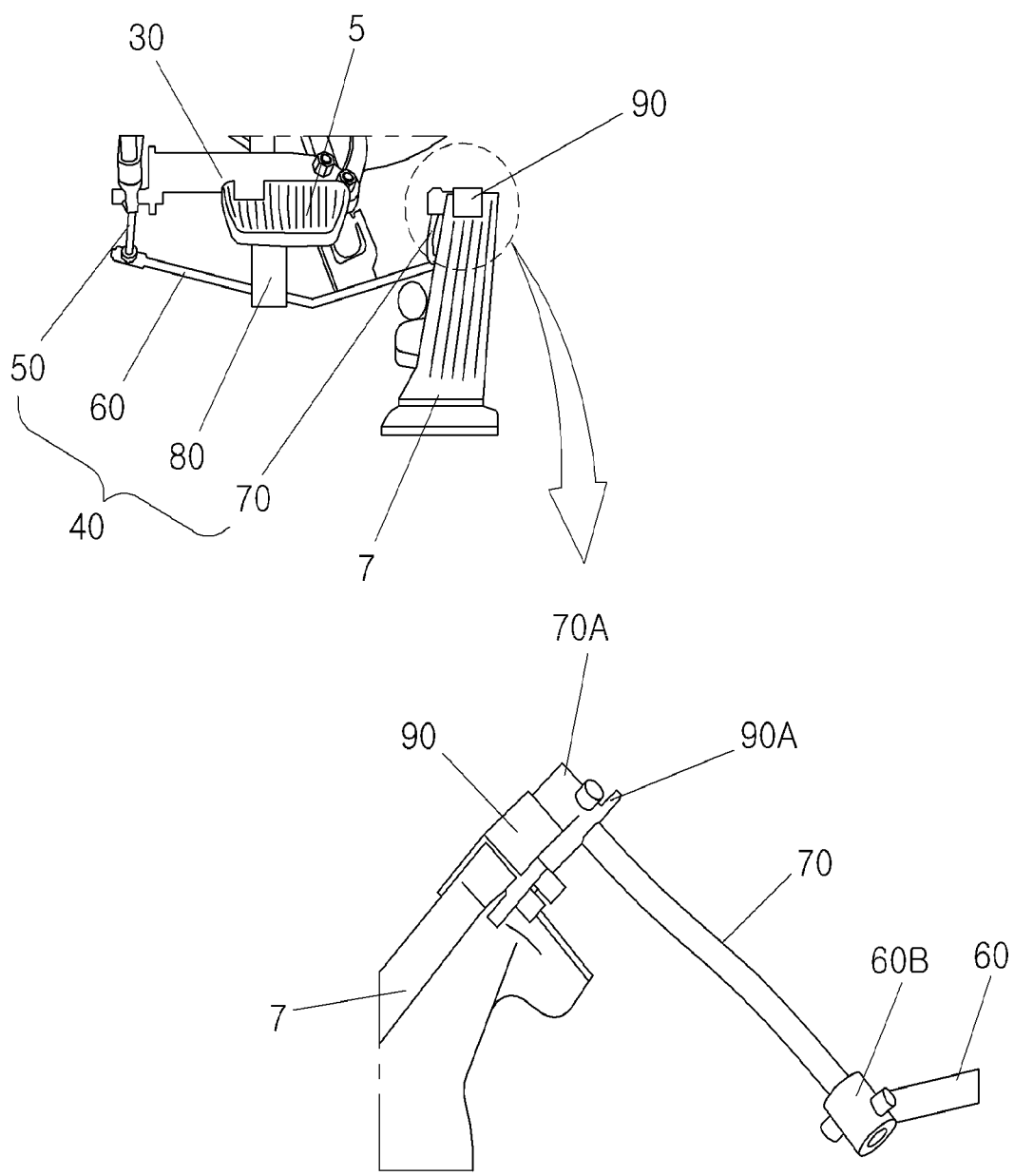
FIG. 6 is a diagram illustrating an accelerator pedal bracket connection structure of the pedal operation link according to an exemplary embodiment of the present invention.

Referring to FIGS. 5 and 6, the accelerator link cable 50 includes an accelerator link damper flange 50A configured to surround the outer tube 23 of the pedal operation link 20 and be over the lower ball joint 20B of the inner tube 21 and a cable of a nylon material configured to be drawn out from the accelerator link damper flange 50A to be connected to the accelerator link 60. In particular, the accelerator link damper flange 50A has substantially a "⌐"-letter shape, is integrated with the outer tube 23 of the pedal operation link 20 by welding, and is fixed to the cable of a nylon material with two screws. Therefore, at the time of pulling or pushing the control bar 10, when the operation force of the outer tube 23 of the pedal operation link 20 is delivered to the accelerator link damper flange 50A, the cable of a nylon material may be pulled by a leverage action of the accelerator link damper flange 50A. Therefore, the cable of a nylon material forms flexibility and a length to absorb the motion of the outer tube 23 along with the inner tube 21. Further, the accelerator link damper flange 50A is further provided with a guide of a plastic material and the guide adheres to the lower ball joint 20B of the inner tube 21, thereby reducing contact noise due to the operation. Therefore, the accelerator link damper flange 50A may have substantially a "⊏"-letter shape.

The accelerator link 60 includes an accelerator link cable connection part 60A configured to be connected to the cable of a nylon material of the accelerator link cable 50 and an accelerator pedal cable connection part 60B connected to the accelerator pedal cable 70, in which a connection section between the accelerator link cable connection part 60A and the accelerator pedal cable connection part 60B is formed with a bent section. In particular, the accelerator link cable connection part 60A and the accelerator pedal cable connection part 60B are each configured of a ball joint. Further, the bent section is formed corresponding to a shape of a space in which the brake pedal 5 and the accelerator pedal 7 are installed.

The accelerator pedal cable 70 made of a nylon material is connected to the accelerator pedal cable connection part 60B of the accelerator link 60 and the other side thereof is provided with an accelerator pedal damper 70A which is fixed to an accelerator link bracket 80 in the state in which it is connected to the accelerator pedal cable connection part 60B. The accelerator pedal damper 70A and the accelerator link bracket 80 are fixed by two screws.

The accelerator link bracket 80 maintains the tension of the accelerator link 60 by disposing an accelerator link ball join 80A in a path through which the accelerator pedal cable 70 passes and allowing the accelerator link ball joint 80A to hold the accelerator pedal cable 70. The accelerator link ball joint 80A is configured of a ball joint. In particular, the accelerator link bracket 80 is fixed to a vehicle body panel at which the steering column 2 is located by using the accelerator link bracket fixing part 80B to stably maintain the motion of the accelerator link 60. The fastening portion for fixing the accelerator link bracket fixing part 80B may use a related part of the brake pedal 5.

The accelerator pedal bracket 90 is fixed by the accelerator pedal damper 70A of the accelerator pedal cable 70 and the screw and an opposite side thereof is provided with an accelerator pad flange 90A having substantially a '⊏'-letter shape to be fitted in the pad portion of the accelerator pedal 7.

Figure 7:
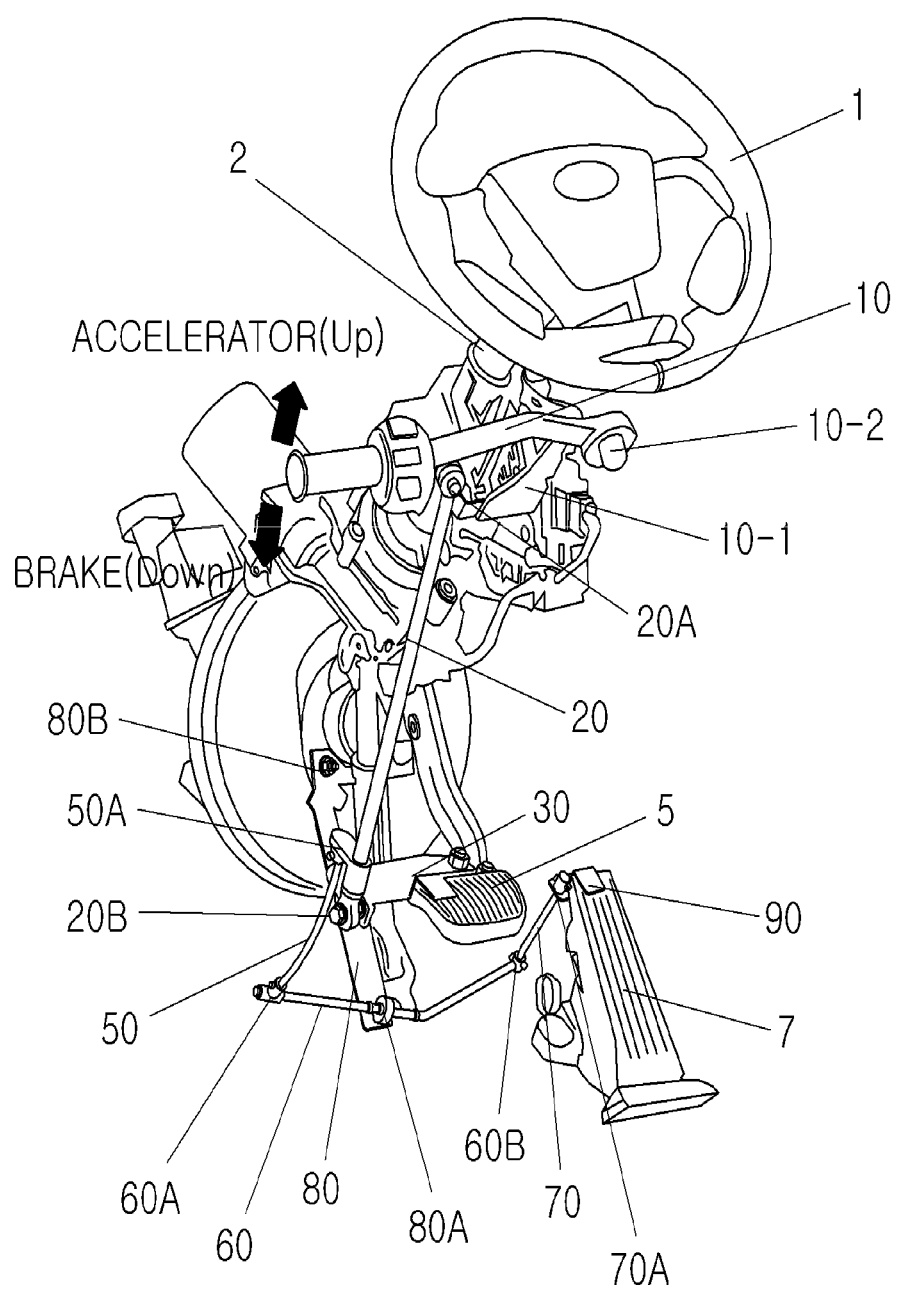
FIG. 7 is a diagram illustrating an accelerator and brake operation state of the single link type drive assistance system for a handicapped person according to an exemplary embodiment of the present invention.

FIG. 7 is a diagram illustrating an accelerator and brake operation state of the single link type drive assistance system for a handicapped person according to an exemplary embodiment of the present invention.

As illustrated in FIG. 7, when the control bar 10 is pulled (accelerator up), a sliding motion of the outer tube 23 of the pedal operation link 20 is delivered to the accelerator link 60 and the accelerator pedal cable 70 by the leverage action of the accelerator link cable 50 to operate the accelerator pedal 7 connected to the accelerator link bracket 80. In this case, the sliding motion of the outer tube 23 brings about the separation of the inner tube 21 from the outer tube 23, and thus even though the accelerator pedal 7 is operated, the brake pedal 5 is not changed.

On the other hand, when the control bar 10 is pushed (brake down), the outer tube 23 delivers a force to the inner tube 21 as it is and thus the brake pedal bracket 30 is applied with a force from the lower ball joint 20B of the inner tube 21 and operates the brake pedal 5. In this case, the nylon material of the accelerator link cable 50 is naturally bent to prevent a force from being delivered to the accelerator link 60, and thus even though the brake pedal 5 is operated, the accelerator pedal 7 is not changed.

Therefore, the inner tube 21 and the outer tube 23 of the pedal operation link 20 deliver the motion of the control bar 1 pushed without the operation of the outer tube 23 at the time of the operation of the brake to the inner tube 21, while the inner tube 21 and the outer tube 23 of the pedal operation link 20 deliver the motion of the control bar 10 pulled without the operation of the inner tube 21 at the time of the operation of the accelerator to the outer tube 23 to be able to differentiate the operation of the acceleration pedal 7 and the brake pedal 5 depending on the pulling (accelerator operation) or the pushing (brake operation).

Figure 8:
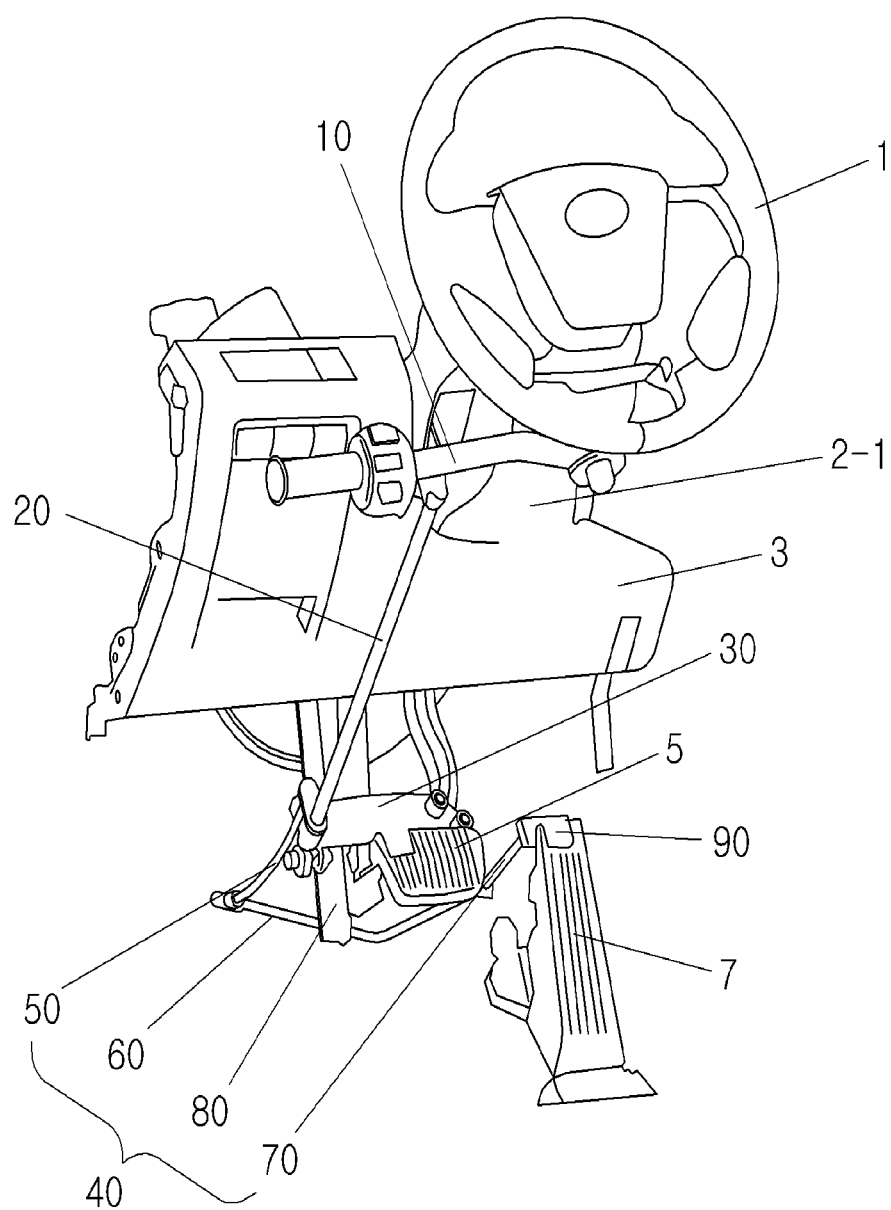
FIG. 8 is an appearance configuration diagram in a state in which a shroud of the single link type drive assistance system for a handicapped person according to an exemplary embodiment of the present invention is mounted.

Meanwhile, FIG. 8 is an appearance configuration diagram in a state in which a shroud of the single link type drive assistance system for a handicapped person according to an exemplary embodiment of the present invention is mounted.

As illustrated in FIG. 8, when the steering column 2 is surrounded with the column tube 2-1 and a shroud panel 3 is mounted, only the control bar 10 and the pedal operation link 20 are exposed to a lower portion of the steering wheel 1. Further, the accelerator link cable 50, the accelerator link 60, the accelerator pedal cable 70, and the accelerator link bracket 80 are located in a hidden space in which the brake pedal 5 and the accelerator pedal 7 are mounted. Therefore, the drive assistance system according to the exemplary embodiment of the present invention has a remarkably beautiful appearance at the time of being actually mounted, and thus the user satisfaction is greatly improved.

In particular, the accelerator pedal 7 and the brake pedal 5 share one pedal operation link 20 connected to the control bar 10 to greatly reduce the risk of injuring a driver due to the plurality of links at the time of collision, the brake operation and the pedal operation are performed by one pedal operation link 20 and the plastic and nylon materials are applied to greatly reduce the "clank" noise, and the connection structure of the brake pedal 5 using the brake pedal brake 30 and the accelerator pedal 7 using the accelerator pedal bracket 90 are applied to perform the sophisticated acceleration and deceleration pedal operation depending on the optimally designed pedal ratio and apply the flow mount type accelerator pedal without the pedal arm.

As described above, the single link type drive assistance system for a handicapped person according to the exemplary embodiment of the present invention includes the control bar 10 configured to make the hinge joint 10B connected to the steering column 2 to form a rotation center at the time of the up and down operations, the pedal operation link 20 configured to include the inner tube 21 connected to the control bar 10 to deliver the down operation force to the brake pedal 5 and the outer tube 23 slidably moving with respect to the inner tube 21 at the time of the up operation, and the accelerator cable unit 40 configured to receive the sliding motion of the outer tube 23 to operate the accelerator pedal 7, thereby improving the collision stability, the noise, and the operability by the control of the accelerator pedal 7 and the brake pedal 5 using one pedal operation link 20, in particular, more improving the marketability due to the beautiful appearance in the state in which the actual shroud panel 3 is mounted.

The present invention has the following effects by configuring the drive assistance apparatus for a handicapped person in the single link structure.

First, it is possible to reduce a risk of injuring a driver in half at the time of collision by applying the operation link in the single link type. Second, it is possible to remarkably reduce the "clank" operation noise generated at the time of sliding due to the application of one link at the time of the operation and improve the customer complaints at the time of the operation due to the additional removal of noise by the application of the guide. Third, it is possible to provide the smooth acceleration and deceleration by applying the guide bracket to the pad of the brake pedal for the sophisticated pedal operation and using the optimally designed pedal ratio using the accelerator bracket mounted at the upper end of the pad of the accelerator pedal as it is. Fourth, it is possible to increase the freedom of design at the time of designing a new car by enabling the single link type drive assistance system to be mounted in the flow mount type accelerator pedal without the pedal arm.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A single link type drive assistance system for a handicapped person, comprising:
   a control bar configured to make a hinge joint connected to a steering column to form a rotation center at time of up and down operations at a lower portion of a steering wheel;

a pedal operation link configured to include an inner tube connected to the control bar to deliver a down operation force using a brake pedal and an outer tube surrounding the inner tube, the outer tube moving along with the inner tube at the time of the down operation to operate the brake pedal and slidably moving with respect to the inner tube without a motion of the inner tube connected to the brake pedal at the time of the up operation; and an accelerator cable unit configured to be applied with a sliding motion of the outer tube to operate an accelerator pedal, wherein the pedal operation link is connected to the control bar by an upper ball joint of the inner tube and is connected to the brake pedal using a brake pedal bracket fixed to a lower ball joint of the inner tube, and wherein the brake pedal bracket is configured to include a pedal operation link fixing part fixed to the lower ball joint, a pedal arm fixing part fastened with an arm portion of the brake pedal, and a brake pad flange pressed to a pad portion of the brake pedal.

2. The system of claim 1, wherein the accelerator cable unit receives the sliding motion of the outer tube through a cable of a nylon material and the cable of a nylon cable has flexibility and length to absorb the motion of the outer tube along with the inner tube.

3. The system of claim 1, wherein the control bar is provided with a handle having a button disposed at an opposite side of the hinge joint, the hinge joint is connected by a column bracket and a hinge bearing fixed to the steering column, and the column bracket and the hinge bearing are covered with a column tube surrounding the steering column.

4. The system of claim 1, wherein the pedal operation link fixing part and the pedal arm fixing part are each fastened with each other by a bolt and the brake pad flange surrounds the pad portion.

5. The system of claim 1, wherein the accelerator cable unit is configured to include an accelerator link cable of a nylon material having flexibility and a length to absorb the motion of the outer tube along with the inner tube and receiving the sliding motion of the outer tube, an accelerator link receiving the motion of the accelerator link cable, an accelerator pedal cable delivering the motion of the accelerator link to an accelerator pedal bracket, and an accelerator link bracket maintaining a tension of the accelerator link.

6. The system of claim 5, wherein the accelerator link cable is provided with an accelerator link damper flange coupled with the outer tube and the accelerator link damper flange is connected to the cable of a nylon material and thus is connected to the accelerator link.

7. The system of claim 6, wherein the accelerator link damper flange has a L-shape to make the cable of a nylon material be spaced apart from the outer tube.

8. The system of claim 7, wherein the accelerator link damper flange is further provided with a guide of a plastic material and has a U-shape.

9. The system of claim 5, wherein the accelerator link is configured to include an accelerator link cable connection part connected to the cable of a nylon material and an accelerator pedal cable connection part connected to the accelerator pedal cable and the accelerator link cable connection part and the accelerator pedal cable connection part are each configured of a ball joint.

10. The system of claim 5, wherein the accelerator pedal cable of the nylon material is connected to the accelerator pedal cable connection part of the accelerator link and the accelerator link bracket is provided with an accelerator pedal damper fixed by a screw.

11. The system of claim 5, wherein the accelerator link bracket is provided with an accelerator link ball joint supporting the accelerator pedal cable and is provided with an accelerator link bracket fixing part fixed to a vehicle body panel at which the steering column is located.

12. The system of claim 5, wherein the accelerator pedal bracket is fixed by the accelerator pedal damper of the accelerator pedal cable and the screw and is provided with an accelerator pad flange fitted in a pad portion of the accelerator pedal.

13. The system of claim 5, wherein the control bar and the pedal operation link are exposed to the outside from a shroud panel surrounding a circumference of the steering column.

* * * * *